US008153557B2

(12) United States Patent
Jensen et al.

(10) Patent No.: US 8,153,557 B2
(45) Date of Patent: Apr. 10, 2012

(54) AGRICULTURALLY USEFUL COMPOSITIONS

(76) Inventors: Jeffrey L. Jensen, Brownsburg, IN (US); Derek J. Hopkins, New Plymouth (NZ); Mark R. Linton, Paraparaumu (NZ)

( * ) Notice: Subject to any disclaimer, the term of this patent is extended or adjusted under 35 U.S.C. 154(b) by 1141 days.

(21) Appl. No.: 11/897,479

(22) Filed: Aug. 30, 2007

(65) Prior Publication Data
US 2008/0058209 A1 Mar. 6, 2008

Related U.S. Application Data

(60) Provisional application No. 60/841,268, filed on Aug. 30, 2006.

(51) Int. Cl.
*A01N 25/00* (2006.01)
*A01N 25/22* (2006.01)
*A01N 25/06* (2006.01)
*A01N 25/10* (2006.01)
*A01N 25/32* (2006.01)
*A01N 65/00* (2009.01)

(52) U.S. Cl. .................................................... 504/105
(58) Field of Classification Search .................. 504/105
See application file for complete search history.

(56) References Cited

U.S. PATENT DOCUMENTS

| 5,688,850 A * | 11/1997 | Wyffels | 524/317 |
| 6,348,434 B1 * | 2/2002 | Schmidt | 504/116.1 |
| 2006/0199736 A1 * | 9/2006 | Vasek | 504/142 |

FOREIGN PATENT DOCUMENTS

| WO | WO 2007/028538 | 3/2007 |
| WO | PCT/US2007/019120 | 12/2008 |

OTHER PUBLICATIONS

PCT/US2007/019120 International Search Report, Mar. 4, 2008, Jeffrey L. Jensen et al. [Dow AgroSciences LLC].
PCT/US2007/019120 Written Opinion, Mar. 4, 2008, Jeffrey L. Jensen et al. [Dow AgroSciences LLC].
PURAC, 2-Ethyxlhexyl-S-Lactate Purasolv® EHL Safety Data Sheet, 2000.
PURAC, Talking Industrial, 2000.
UNIQUEMA, Atlox® Polymeric Surfactants: Agriculutural Applications, Technical Bulletin 00-4, 2000.
UNIQUEMA; ATLAS G5000 Product Details, 2002.

* cited by examiner

*Primary Examiner* — Fereydoun G Sajjadi
*Assistant Examiner* — Courtney Brown
(74) *Attorney, Agent, or Firm* — Craig E. Mixan; Carl D. Corvin

(57) ABSTRACT

A composition comprising at least one aromatic compound and at least one lactate ester compound is provided. Optionally, said composition can further comprise Cloquintocet-mexyl. Optionally, said composition can further comprise at least one emulsifier. Optionally, said composition can further comprise at least one herbicide. Processes comprising mixing such components are provided. Processes for controlling weeds or grasses or both with such compositions are provided.

4 Claims, No Drawings

AGRICULTURALLY USEFUL COMPOSITIONS

CROSS-REFERENCE TO RELATED APPLICATIONS

This application claims priority from provisional application 60/841,268 filed in the United States Patent Office on Aug. 30, 2006.

BACKGROUND OF THE INVENTION

The field of this invention is agriculturally useful compositions.

Cloquintocet-mexyl has the following structural formula.

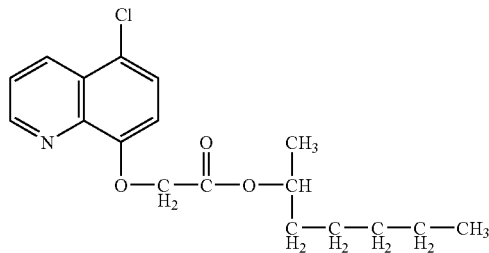

It is known to function as a herbicide safener. In general, a herbicide safener is a compound that reduces the effects of the herbicide when applied to crops.

One means of formulating cloquintocet-mexyl for use in agriculture would be as a liquid concentrate. An example would be an emulsifiable concentrate ("EC") comprising cloquintocet-mexyl, an organic solvent, and an emulsifier that can then be tank mixed with a separate herbicidal product that comprises a herbicide and water. The organic solvent could also comprise other active ingredients or even more of the same active ingredient that is in the water phase. Other compositions comprising cloquintocet-mexyl are possible such as "oil dispersions" (OD), "suspo emulsions" (SE), "emulsions in water" (EW), however, common to all of these systems though, is that cloquintocet-mexyl is solubilized in an organic component.

Cloquintocet-mexyl will easily convert to its hydrate when it comes into contact with water. Cloquintocet-mexyl hydrate will then precipitate as large crystals that will hinder the mixture's sprayability and subsequently its ability to function as a herbicide safener. This invention provides a solution to this problem.

SUMMARY OF THE INVENTION

A composition comprising at least one aromatic compound and at least one lactate ester compound is provided. Optionally, said composition can further comprise Cloquintocet-mexyl. Optionally, said composition can further comprise at least one emulsifier. Optionally, said composition can further comprise at least one herbicide. Processes comprising mixing such components are provided. Processes for controlling weeds or grasses or both with such compositions are provided.

DETAILED DESCRIPTION OF THE INVENTION

Aromatic Compound

Any aromatic compound can be used in this invention. For example, aromatic hydrocarbons can be used. Also, heteroaromatic compounds can be used. Suitable aromatic hydrocarbons usually have from about 7 to about 18 carbon atoms. Suitable aromatic hydrocarbons include, but are not limited to, mono, di, and tri, alkylbenzenes, as well as, naphthalene and mono or poly-alkyl substituted naphthalenes. Additionally other substituted aromatic compounds can be used such as, aromatic aldehydes with a molecule weight in the range of about 100 to about 200 Daltons and aromatic ketones with a molecular weight of about 100 to 300 Daltons. Furthermore, mixtures of various aromatic compounds can be used. For example, a mixture of mono, di, and tri alkylbenzenes and substituted naphthalenes may be used. In general, the weight percent of aromatic compound to lactate ester compound based on the total weight of aromatic compound plus the lactate ester compound is show in Table W.

TABLE W

| | Weight Percent based on total weight of Aromatic Compound + Lactate Ester Compound | | |
|---|---|---|---|
| | Broad Range | Middle Range | Narrow Range |
| Aromatic Compound | about 13-87% | about 25-75% | about 35-65% |
| Lactate Ester Compound | about 87-13% | about 75-25% | about 65-35% |

Lactate Ester Compound

Any lactate ester compound can be used in this invention. For example alkyl lactate ester compounds may be used. The alkyls can be branched or un-branched alkyls containing from 1 to about 12 carbon atoms. The alkyls can be substituted with various functional groups provided that such functional groups do not interfere with the physical properties of the final desired mixture. Suitable alkyl lactate compounds include, but are not limited to, the compounds in Table L.

TABLE L

| | |
|---|---|
| $CH_3CH_2OCOOCH_3$ | methyl lactate |
| $CH_3CH_2OCOOCH_2CH_3$ | ethyl lactate |
| $CH_3CH_2OCOOCH_2CH_2CH_3$ | n-propyl lactate |
| $CH_3CH_2OCOOCH_2(CH_3)_2$ | isopropyl lactate |
| $CH_3CH_2OCOOCH_2CH_2CH_2CH_3$ | n-butyl lactate |
| $CH_3CH_2OCOOCH_2CH(C_2H_5)CH_2CH_2CH_2CH_3$ | 2-ethylhexyl lactate |

Additionally, it should be noted that optical isomers of various lactates may be used to good effect.

Lactate Ester/Lactic Acid Blend

Upon exposure to water, it is possible for the lactate ester compounds used in this invention to undergo hydrolysis to lactic acid. If this occurs in a composition of this invention, the weight ratio of lactate ester compounds to lactic acid compounds is from about 1:1000 to about 1:0.0001.

Cloquintocet-mexyl

When a composition comprising at least one aromatic compound, at least one lactate ester compound, and Cloquintocet-mexyl, is desired, the weight ratio of aromatic compounds to Cloquintocet-mexyl is from about 1:1000 to about 1:0.0001 and the weight ratio of lactate ester compound to Cloquntocet-mexyl is from about 1:1000 to about 1:0.0001

Emulsifier

Any emulsifier can be used in this invention. The amount of emulsifier to use can vary widely, however, in general, the weight percent is in the range of about 2 to about 20 weight percent based on the total weight of the composition. Suitable examples are surface-active agents (surfactants) of nonionic, cationic, or anionic, construction having good emulsifying, dispersing, and wetting properties. Surfactants will also be understood as comprising mixtures of surfactants.

Suitable anionic surfactants may be water-soluble soaps, as well as, water-soluble synthetic surface-active compounds.

Suitable soaps are the alkali metal salts, alkaline earth metal salts, ammonium salts, or substituted ammonium salts of higher fatty acids (C10-C22), e.g. the sodium or potassium salts of oleic, stearic acid, or of natural fatty acid mixtures which can be obtained from coconut oil or tallow oil. Further suitable soaps are also the fatty acid methyl taurin salts.

Synthetic surfactants can be used in this invention such as fatty sulfonates, fatty sulfates, sulfonated benzimidazole derivatives, or alkylarylsulfonates.

The fatty alcohol sulfonates or sulfates, are usually in the form of alkali metal salts, alkaline earth metal salts, ammonium salts, or substituted ammonium salts, and they contain a C8-C22 alkyl radical that also includes the alkyl moiety of acyl radicals, e.g. the sodium or calcium salt of ligninsulfonic acid, of dodecylsulfate, or of a mixture of fatty alcohol sulfates obtained from natural fatty acids. These compounds also comprise the salts of sulfated or sulfonated fatty alcohol and ethylene oxide adducts. The sulfonated benz-imidazole derivatives preferably contain 2 sulfonic acid groups and one fatty acid radical containing 8 to 22 carbon atoms. Illustrative examples of alkylarylsulfonates are the sodium, calcium, or triethanolamine salts of dodecylbenzenesulfonic acid, dibutylnaphthalenesulfonic acid, or of a condensate of naphthalenesulfonic acid and formaldehyde.

Corresponding phosphates, typically salts of the phosphoric acid ester of an adduct of p-nonylphenol with 4 to 14 mol of ethylene oxide, or phospholipids, are also suitable.

Nonionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable nonionic surfactants are the water-soluble polyadducts of polyethylene oxide with polypropylene glycol, ethylenediaminopolypropylene glycol and alkylpolypropylene glycol containing 1 to 10 carbon atoms in the alkyl chain, which polyadducts contain 20 to 250 ethylene glycol ether groups and 10 to 100 propylene glycol ether groups. These compounds usually contain 1 to 5 ethylene glycol units per propylene glycol unit.

Illustrative examples of nonionic surfactants are polyalkylene glycol ethers nonylphenol polyethoxylates, polyethoxylated castor oil, polyadducts of polypropylene and polyethylene oxide (to include random copolymers, block copolymers, graft copolymers), tributylphenol polyethoxylate, polyethylene glycol and octylphenol polyethoxylate.

Fatty acid esters of polyoxyethylene sorbitan are also suitable nonionic surfactants, typically polyoxyethylene sorbitan trioleate.

Cationic surfactants are preferably quaternary ammonium salts carrying, as N-substituent, at least one C8-C22 alkyl radical and, as further substituents, optionally halogenated lower alkyl, benzyl or hydroxy-lower alkyl radicals. The salts are preferably in the form of halides, methyl sulfates or ethyl sulfates, for example stearyl trimethylammonium chloride or benzyl bis(2-chloroethyl) ethylammonium bromide.

Other surfactants employed in the art of formulation are described, in "McCutcheon's Detergents and Emulsifiers Volume 1: International and North American Editions", The Manufacturing Confectioner Publishing Co., Glen Rock, N.J., 2006, H. Stache, "Tensid-Taschenbuch" (Handbook of Surfactants), Carl Hanser Verlag, Munich/Vienna 1981, and M. and J. Ash, "Encyclopedia of Surfactants", Vol I-III, Chemical Publishing Co., New York, 1980-81.

Herbicides

Any herbicide can be used in this invention. Suitable examples of herbicides that can be used are:

amide herbicides such as allidochlor, beflubutamid, benzadox, benzipram, bromobutide, cafenstrole, CDEA, chlorthiamid, cyprazole, dimethenamid, dimethenamid-P, diphenamid, epronaz, etnipromid, fentrazamide, flupoxam, fomesafen, halosafen, isocarbamid, isoxaben, napropamide, naptalam, pethoxamid, propyzamide, quinonamid, and tebutam;

anilide herbicides such as chloranocryl, cisanilide, clomeprop, cypromid, diflufenican, etobenzanid, fenasulam, flufenacet, flufenican, mefenacet, mefluidide, metamifop, monalide, naproanilide, pentanochlor, picolinafen, and propanil;

arylalanine herbicides such as benzoylprop, flamprop, and flamprop-M;

chloroacetanilide herbicides such as acetochlor, alachlor, butachlor, butenachlor, delachlor, diethatyl, dimethachlor, metazachlor, metolachlor, S-metolachlor, pretilachlor, propachlor, propisochlor, prynachlor, terbuchlor, thenylchlor, and xylachlor;

sulfonanilide herbicides such as benzofluor, perfluidone, pyrimisulfan and profluazol;

sulfonamide herbicides such as asulam, carbasulam, fenasulam, and oryzalin;

antibiotic herbicides such as bilanafos;

benzoic acid herbicides such as chloramben, dicamba, 2,3,6-TBA, and tricamba;

pyrimidinyloxybenzoic acid herbicides such as bispyribac and pyriminobac;

pyrimidinylthiobenzoic acid herbicides such as pyrithiobac;

phthalic acid herbicides such as chlorthal;

picolinic acid herbicides such as aminopyralid, clopyralid, and picloram;

quinolinecarboxylic acid herbicides such as quinclorac and quinmerac;

arsenical herbicides such as cacodylic acid, CMA, DSMA, hexaflurate, MAA, MAMA, MSMA, potassium arsenite, and sodium arsenite;

benzoylcyclohexanedione herbicides such as mesotrione, sulcotrione, tefuryltrione and tembotrione;

benzofuranyl alkylsulfonate herbicides such as benfuresate and ethofumesate;

carbamate herbicides such as asulam, carboxazole chlorprocarb, dichlormate, fenasulam, karbutilate, and terbucarb;

carbanilate herbicides such as barban, BCPC, carbasulam, carbetamide, CEPC, chlorbufam, chlorpropham, CPPC, desmedipham, phenisopham, phenmedipham, phenmedipham-ethyl, propham, and swep;

cyclohexene oxime herbicides such as alloxydim, butroxydim, clethodim, cloproxydim, cycloxydim, profoxydim, sethoxydim, tepraloxydim, and tralkoxydim;

cyclopropylisoxazole herbicides such as isoxachlortole and isoxaflutole;

dicarboximide herbicides such as benzfendizone, cinidon-ethyl, flumezin, flumiclorac, flumioxazin, and flumipropyn;

dinitroaniline herbicides such as benfluralin, butralin, dinitramine, ethalfluralin, fluchloralin, isopropalin, methalpropalin, nitralin, oryzalin, pendimethalin, prodiamine, profluralin, and trifluralin;

dinitrophenol herbicides such as dinofenate, dinoprop, dinosam, dinoseb, dinoterb, DNOC, etinofen, and medinoterb;

diphenyl ether herbicides such as ethoxyfen;

nitrophenyl ether herbicides such as acifluorfen, aclonifen, bifenox, chlomethoxyfen, chlornitrofen, etnipromid, fluorodifen, fluoroglycofen, fluoronitrofen, fomesafen, furyloxyfen, halosafen, lactofen, nitrofen, nitrofluorfen, and oxyfluorfen;

dithiocarbamate herbicides such as dazomet and metam;

halogenated aliphatic herbicides such as alorac, chloropon, dalapon, flupropanate, hexachloroacetone, iodomethane, methyl bromide, monochloroacetic acid, SMA, and TCA;

imidazolinone herbicides such as imazamethabenz, imazamox, imazapic, imazapyr, imazaquin, and imazethapyr;

inorganic herbicides such as ammonium sulfamate, borax, calcium chlorate, copper sulfate, ferrous sulfate, potassium azide, potassium cyanate, sodium azide, sodium chlorate, and sulfuric acid;

nitrile herbicides such as bromobonil, bromoxynil, chloroxynil, dichlobenil, iodobonil, ioxynil, and pyraclonil;

organophosphorus herbicides such as amiprofos-methyl, anilofos, bensulide, bilanafos, butamifos, 2,4-DEP, DMPA, EBEP, fosamine, glufosinate, glyphosate, and piperophos;

phenoxy herbicides such as bromofenoxim, clomeprop, 2,4-DEB, 2,4-DEP, difenopenten, disul, erbon, etnipromid, fenteracol, and trifopsime;

phenoxyacetic herbicides such as 4-CPA, 2,4-D, 3,4-DA, MCPA, MCPA-thioethyl, and 2,4,5-T;

phenoxybutyric herbicides such as 4-CPB, 2,4-DB, 3,4-DB, MCPB, and 2,4,5-TB;

phenoxypropionic herbicides such as cloprop, 4-CPP, dichlorprop, dichlorprop-P, 3,4-DP, fenoprop, mecoprop, and mecoprop-P;

aryloxyphenoxypropionic herbicides such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P, and trifop;

phenylenediamine herbicides such as dinitramine and prodiamine;

phenyl pyrazolyl ketone herbicides such as benzofenap, pyrazolynate, pyrasulfotole, pyrazoxyfen, and topramezone;

pyrazolylphenyl herbicides such as fluazolate and pyraflufen;

pyridazine herbicides such as credazine, pyridafol, and pyridate;

pyridazinone herbicides such as brompyrazon, chloridazon, dimidazon, flufenpyr, metflurazon, norflurazon, oxapyrazon and pydanon;

pyridine herbicides such as aminopyralid, cliodinate, clopyralid, dithiopyr, fluroxypyr, haloxydine, picloram, picolinafen, pyriclor, thiazopyr, and triclopyr;

pyrimidinediamine herbicides such as iprymidam and tioclorim;

quaternary ammonium herbicides such as cyperquat, diethamquat, difenzoquat, diquat, morfamquat, and paraquat;

thiocarbamate herbicides such as butylate, cycloate, diallate, EPTC, esprocarb, ethiolate, isopolinate, methiobencarb, molinate, orbencarb, pebulate, prosulfocarb, pyributicarb, sulfallate, thiobencarb, tiocarbazil, tri-allate, and vernolate;

thiocarbonate herbicides such as dimexano, EXD and proxan;

thiourea herbicides such as methiuron;

triazine herbicides such as dipropetryn, triaziflam, and trihydroxytriazine;

chlorotriazine herbicides such as atrazine, chlorazine, cyanazine, cyprazine, eglinazine, ipazine, mesoprazine, procyazine, proglinazine, propazine, sebuthylazine, simazine, terbuthylazine, and trietazine;

methoxytriazine herbicides such as atraton, methometon, prometon, secbumeton, simeton, and terbumeton;

methylthiotriazine herbicides such as ametryn, aziprotryne, cyanatryn, desmetryn, dimethametryn, methoprotryne, prometryn, simetryn and terbutryn;

triazinone herbicides such as ametridione, amibuzin, hexazinone, isomethiozin, metamitron, and metribuzin;

triazole herbicides such as amitrole, cafenstrole, epronaz, and flupoxam;

triazolone herbicides such as amicarbazone, bencarbazone, carfentrazone, flucarbazone, propoxycarbazone, sulfentrazone, and thiencarbazone-methyl;

triazolopyrimidine herbicides such as cloransulam, diclosulam, florasulam, flumetsulam, metosulam, penoxsulam, and pyroxsulam;

uracil herbicides such as butafenacil, bromacil, flupropacil, isocil, lenacil, and terbacil;

3-phenyluracils;

urea herbicides such as benzthiazuron, cumyluron, cycluron, dichloralurea, diflufenzopyr, isonoruron, isouron, methabenzthiazuron, monisouron, and noruron;

phenylurea herbicides such as anisuron, buturon, chlorbromuron, chloreturon, chlorotoluron, chloroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, neburon, parafluron, phenobenzuron, siduron, tetrafluron, and thidiazuron;

pyrimidinylsulfonylurea herbicides such as amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, nicosulfuron, orthosulfamuron, oxasulfuron, primisulfuron, pyrazosulfuron, rimsulfuron, sulfometuron, sulfosulfuron, and trifloxysulfuron;

triazinylsulfonylurea herbicides such as chlorsulfuron, cinosulfuron, ethametsulfuron, iodosulfuron, metsulfuron, prosulfuron, thifensulfuron, triasulfuron, tribenuron, triflusulfuron, and tritosulfuron;

thiadiazolylurea herbicides such as buthiuron, ethidimuron, tebuthiuron, thiazafluron and thidiazuron; and unclassified herbicides such as acrolein, allyl alcohol, azafenidin, benazolin, bentazone, benzobicyclon, buthidazole, calcium cyanamide, cambendichlor, chlorfenac, chlorfenprop, chlorflurazole, chlorflurenol, cinmethylin, clomazone, CPMF, cresol, ortho-dichlorobenzene, dimepiperate, endothal, fluoromidine, fluridone, flurochloridone, flurtamone, fluthiacet, indanofan, methazole, methyl isothiocyanate, nipyraclofen, OCH, oxadiargyl, oxadiazon, oxaziclomefone, pentachlorophenol, pentoxazone, phenylmercury acetate, pinoxaden, prosulfalin, pyribenzoxim, pyriftalid, quinoclamine, rhodethanil, sulglycapin, thidiazimin, tridiphane, trimeturon, tripropindan, and tritac.

Additionally, as further examples, herbicides includes the herbicides disclosed in U.S. Pat. No. 6,559,101.

An additional example of a herbicide useful in this invention has the following structural formula.

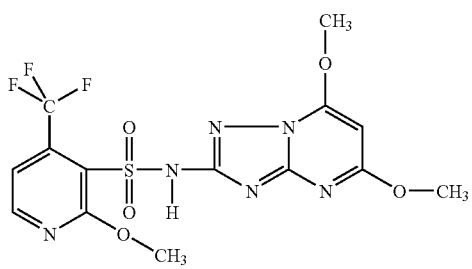

It is also known as N-(5,7-dimethoxy[1,2,4]triazolo[1,5-a]pyrimidin-2-yl)-2-methoxy-4-(trifluoromethyl)-3-pyridinesulfonamide. It has a CAS Registry Number of 422556-08-9. It is available from Dow AgroSciences LLC.

It is also contemplated that one or more herbicides can be used at the same time in this invention. Additionally, agriculturally acceptable salts of these herbicides can also be used.

Preparation

The compositions of this invention can be mixed together in any conventional manner.

Applications

A composition comprising a mixture of an aromatic compound and a lactate ester compound can be a stand alone that can be sold so that such stand alone can be mixed with other components in order to produce a desired mixture that can be used for agricultural purposes.

A composition comprising a mixture of an aromatic compound, a lactate ester compound, and Cloquintocet-mexyl, can be a stand alone that can be sold so that such stand alone can be mixed with other components in order to produce a desired mixture that can be used for agricultural purposes.

A composition comprising a mixture of an aromatic compound, a lactate ester compound, Cloquintocet-mexyl, and an emulsifier, can be a stand alone that can be sold so that such stand alone can be mixed with other components in order to produce a desired mixture that can be used for agricultural purposes.

The herbicidal compositions herein can be used in controlling or as an aid in controlling weeds or grasses or both in crops of cultivated plants, typically in crops of cereals, rape, sugar beet, sugar cane, plantations, rice, cotton and, preferably, in crops of maize and soybean. Such compositions are suitable for all standard methods of application used in agriculture, typically preemergence application and postemergence application. The rate of application can vary over a wide range and will depend on the nature of the soil, the type of application (pre- or postemergence), application to the seed furrow; no tillage application etc.), the cultivated plant, the weed to be controlled, the respective prevailing climatic conditions; and on other factors governed by the type of application, time of application and the target crop.

The concentration of the active ingredients in the herbicidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with a carrier, such as water, before application. The diluted compositions usually applied to weeds or the locus of weeds generally contain about 0.001 to about 5 weight percent active ingredient and preferably contain about 0.01 to about 0.5 percent.

The term herbicide is used herein to mean an active ingredient that controls or adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation are meant to include germinant seeds, emerging seedlings and established vegetation.

Herbicidal activity is exhibited by the compounds of the present invention when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non selective or selective herbicidal action.

Application rates of about 0.001 to about 1 kg/ha are generally employed in postemergence operations; for preemergence applications, rates of about 0.01 to about 2 kg/ha are generally employed. The higher rates designated generally give non-selective control of a broad variety of undesirable vegetation. The lower rates typically give selective control and, by judicious election of compounds, timing, and rates of application, can be employed in the locus of crops.

EXAMPLES

The following examples are provided to further illustrate the invention and are not to limited the scope of the invention.

Example One

The Following Items where Mix Together (See Table E1).

TABLE E1

| Item | Weight Percent |
| --- | --- |
| Aromatic 200 | 15.3 |
| n-Butyl Lactate | 15.3 |
| ATLOX ® 4914 | 1.4 |
| Cloquintocet-mexyl | 4.2 |
| ATLAS ® G-5000 | 2.2 |
| Water | 61.6 |

ATLOX 4914® T 36 (registered trademark of Unichema Chemie BV) is an alkyd-PEG resin and is used as an emulsifier. It is available from Unichema Chemie BV.

ATLAS G-5000® F (registered trademark of Unichema Chemie BV) is a hydrophilic AB block copolymer and used as an emulsifier. It is available from Unichema Chemie BV.

The Cloquintocet-mexyl was dissolved into a mixture of Aromatic 200 and n-butyl lactate. The emulsifiers were then mixed into the mixture. Finally, water was added and the mixture was turned into a emulsified concentrate (EW) by mechanical stirring. Precipitation of Cloquintocet-mexyl hydrate was not observed.

Example Two

TABLE E2

| CQC Wt % | A200 100% | BL 100% | A200 (88%) + BL (12%) | A200 (50%) + BL (50%) | A200 (12%) + BL (88%) |
|---|---|---|---|---|---|
| 15.5 | P | P | P | P | P |
| 14 | | | P | S | P |
| 13 | | P | | | |
| 12 | | | P | S | P |
| 11 | | P | | | |
| 10 | P | | | | |
| 9 | | P | | | |
| 8 | P | | | | |
| 7 | | P | | | |
| 6 | S | | | | |
| 5 | | S | | | |
| 4 | S | | | | |
| 3 | | S | | | |

In Table E2
"A200" means Aromatic 200.
"BL" means n-butyl lactate.
"CQC" means the weight percent of Cloquintocet-mexyl in solution based on the weight of A200 + BL + CQC before the addition of water.
"P" means that Cloquintocet-mexyl hydrate precipitated from the mixture.
"S" means that Cloquintocet-mexyl hydrate did not precipitated from the mixture.

CQC was dissolved into A200, BL, or a mixture of A200+BL. Thereafter, about 10 weight percent water was added to each sample based on the weight of the sample (A200+BL+CQC). Each sample was prepared at 4° C.

Each of A200(100%) and BL(100%) could only have less than 7 weight percent CQC when mixed with water in order to keep Cloquintocet-mexyl hydrate in solution. However, a 50/50 mixture of A200 and BL synergistically kept up to about 14 weight percent CQC in solution.

We claim:

1. A composition comprising:
   (a) from 85 to 93 weight percent of a blend of (i) at least one aromatic compound selected from the group consisting of mono-, di- or tri-alkylbenzene, unsubstituted or mono- or poly-alkyl substituted naphthalene, and mixtures thereof, and (ii) at least one alkyl lactate ester, in which the ratio of (i) to (ii) on a weight percent basis is from 35:65 to 65:35; and
   (b) from 7 to 15 weight percent of cloquintocet-mexyl.

2. The composition of claim 1 further comprising at least one emulsifier.

3. The composition of claim 1 or 2 further comprising at least one herbicide.

4. A method of preventing precipitation of cloquintocet-mexyl hydrate when cloquintocet-mexyl comes into contact with water comprising dissolving the cloquintocet-mexyl in a blend of (i) at least one aromatic compound selected from the group consisting of mono-, di- or tri-alkylbenzene, unsubstituted or mono- or poly-alkyl substituted naphthalene, and mixtures thereof, and (ii) at least one alkyl lactate ester, in which the ratio of (i) to (ii) on a weight percent basis is from 35:65 to 65:35.

* * * * *